United States Patent
Yada et al.

(10) Patent No.: US 6,910,511 B2
(45) Date of Patent: Jun. 28, 2005

(54) METHOD OF SUPPLYING AMBIENT GAS

(75) Inventors: Shuhei Yada, Mie (JP); Masayasu Goriki, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/849,911

(22) Filed: May 21, 2004

(65) Prior Publication Data

US 2004/0222236 A1 Nov. 11, 2004

Related U.S. Application Data

(63) Continuation of application No. PCT/JP02/12008, filed on Nov. 18, 2002.

(30) Foreign Application Priority Data

Nov. 21, 2001 (JP) .................................... 2001-356288

(51) Int. Cl.[7] .............................................. B65B 1/04
(52) U.S. Cl. ........................................ 141/83; 141/67
(58) Field of Search ............................. 141/1, 9, 100, 141/67, 64, 2, 18

(56) References Cited

U.S. PATENT DOCUMENTS

2001/0025120 A1    9/2001   Shingai et al.

FOREIGN PATENT DOCUMENTS

| JP | 49-95905 | 9/1974 |
|----|----------|--------|
| JP | 2000-256221 | 9/2000 |

Primary Examiner—Steven O. Douglas
(74) Attorney, Agent, or Firm—Oblon, Spivak, McClelland, Maier & Neustadt, P.C.

(57) ABSTRACT

A subject for the invention is to stably supply an ambient gas having a given composition to a production apparatus or storage apparatus for a compound necessitating strict ambient gas regulation during the production, storage, or handling thereof, such as (meth)acrylic acid or an ester thereof which are easily polymerizable and form an explosive composition at ordinary temperature, in a manner not influenced by fluctuations in the amount of the gas used.

In the invention, the pressure of the gas-phase part in a tank (1) or mixing vessel (2) is detected with a manometer (P-1) or (P-2), and a dry air/nitrogen mixed gas is supplied to the tank (1) or mixing vessel (2) in an amount compensating for the gas consumption. The pressure in a mixed-gas supply piping (5) is detected with a manometer (P-5), and a dry air/nitrogen mixed gas is supplied to the piping (5) in an amount compensating for the gas consumption. The degree of opening of a flow control valve (V-4) for nitrogen is regulated so as to be in proportion to the degree of opening of a flow control valve (V-3) for dry air. Thus, a mixed gas having a given oxygen concentration is supplied.

12 Claims, 2 Drawing Sheets

METHOD OF SUPPLYING AMBIENT GAS

TECHNICAL FIELD

The present invention relates to a method of supplying an ambient gas. More particularly, the invention relates to a method for stably supplying, without fail, an ambient gas having a given composition to a production apparatus or storage apparatus for a compound necessitating strict ambient gas regulation during the production, storage, or handling thereof, such as (meth)acrylic acid or an ester thereof.

BACKGROUND ART (Meth)acrylic acid (The term (meth)acrylic acid in this description implies "acrylic acid or methacrylic acid".) or esters thereof are easily polymerizable compounds, and are compounds which form an explosive composition at around ordinary temperature, usually from 0 to 50° C. It is therefore necessary to keep the oxygen concentration in the gas-phase part in the production apparatus or storage apparatus for such compounds at a value within a given range. Namely, oxygen concentrations in the ambient gas lower than the given range result in the occurrence of polymerization reaction, while oxygen concentrations therein higher than the range result in the formation of an explosive composition.

An object of the invention is to provide a method of supplying an ambient gas by which an ambient gas having a given composition can be stably supplied to a production apparatus or storage apparatus for a compound necessitating strict ambient gas regulation during the production, storage, or handling thereof, such as (meth)acrylic acid or an ester thereof which are easily polymerizable and form an explosive composition at ordinary temperature, in a manner not influenced by fluctuations in the amount of the gas used.

DISCLOSURE OF THE INVENTION

The method of supplying an ambient gas of the invention is a method of supplying an ambient gas to a production apparatus and/or storage apparatus for at least one compound from a gas supply source through a supply line, characterized in that a gas consumption in the gas-phase part in the apparatus is detected and, based on the results of this detection, the ambient gas is supplied from the supply line in an amount compensating for the gas consumption in the gas-phase part, and that a gas consumption in the supply line is detected and, based on the results of this detection, the ambient gas is supplied to the supply line from the gas supply source in an amount compensating for the gas consumption in the supply line.

In the invention, an ambient gas is supplied based on a gas consumption in the gas-phase part in an amount compensating for this gas consumption. Because of this, the ambient gas is supplied so that the pressure of this gas-phase part is kept at a constant value. Furthermore, since an ambient gas is supplied from a gas supply source based on a gas consumption in the supply line in an amount compensating for this gas consumption, the ambient gas is supplied so that the pressure in this supply line is kept at a constant value. Thus, the ambient gas pressures of the gas-phase part and in the supply line are kept constant and, in addition, the oxygen concentration in the ambient gas is regulated so as to be constant by regulating the ratio of the flow rate of an incombustible gas to that of air or oxygen. Consequently, an ambient gas having a given composition can be stably supplied according to fluctuations in the amount of the ambient gas used.

In the invention, the ambient gas preferably is a mixed gas comprising an incombustible gas, preferably nitrogen gas, and either air or oxygen.

Examples of the at least one compound which is produced by or stored in the production apparatus or storage apparatus supplied with such ambient gas (Hereinafter, that compound is sometimes referred to as "compound to be sealed".) include compounds which are easily polymerizable and capable of forming an explosive composition at from 0 to 50° C. or easily polymerizable compounds which are inhibited from polymerizing by the oxygen present in the ambient gas. Especially preferred is (meth)acrylic acid or an ester thereof.

It is preferred in the invention that the gas consumption in the gas-phase part or supply line be detected by measuring the pressure of the gas-phase part or in the supply line.

Furthermore, in the case where a mixed gas comprising an incombustible gas and either air or oxygen is supplied as the ambient gas, it is preferred that the incombustible gas and the air or oxygen be separately supplied to the supply line so as to result in a given proportion. In this case, the ratio of the flow rate of the incombustible gas to that of the air or oxygen may be regulated, or the incombustible-gas concentration or oxygen concentration in the supply line may be regulated.

Figure 1:
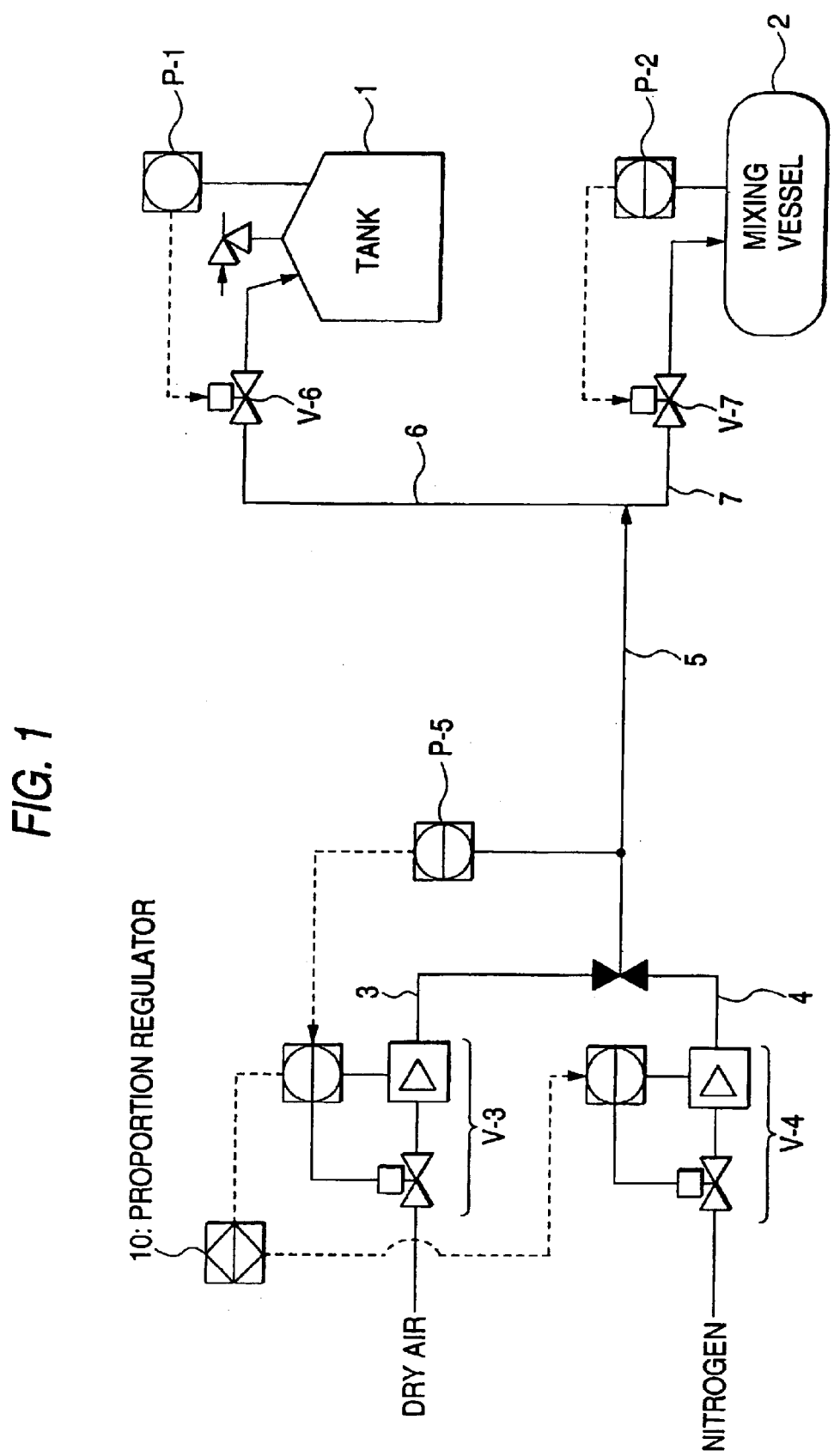
FIG. 1 is a system diagram showing an embodiment of the method of supplying an ambient gas of the invention.

Incidentally, numerals and signs in the drawings are as follows: 1 denotes a tank, 2 a mixing vessel, 10 a proportion regulator, P-1, P-2, and P-5 a manometer, O-5 an oxygen concentration meter, V-3 and V-4 a flow control valve, and V-6 and V-7 an on-off valve.

BEST MODE FOR CARRYING OUT THE INVENTION

Modes for carrying out the method of supplying an ambient gas of the invention will be explained below in detail.

The compound to be sealed in the invention preferably is an easily polymerizable compound capable of forming an explosive composition at from 0 to 50° C. or an easily polymerizable compound which is inhibited from polymerizing by the oxygen present in the ambient gas. Examples of such compounds include (meth)acrylic acid or esters thereof. However, the compound to be sealed should not be construed as being limited to these examples in any way. Examples of the esters of (meth)acrylic acid include methyl acrylate, ethyl acrylate, butyl acrylate, methyl methacrylate, ethyl methacrylate, and the like.

The compound to be sealed may be a mixture of two or more easily polymerizable compounds of the kind shown above or may be a mixture of one of more such easily polymerizable compounds and one or more other compounds.

Usually, the easily polymerizable compound is produced as a composition which is a mixture thereof with a polymerization inhibitor and/or polymerization retarder and optionally with a solvent therefor, and this composition is stored as a product. As the polymerization inhibitor is used a phenol compound such as hydroquinone or methoquinone (hydroquinone monomethyl ether) or a phenothiazine compound such as phenothiazine, bis((α-methylbenzyl) phenothiazine, 3,7-dioctylphenothiazine, or bis(α-dimethylbenzyl)-phenothiazine. The polymerization inhibitor or polymerization retarder should not be construed as being limited in any way to these compounds shown as examples. Two or more of these may be used in combination.

As the solvent for the polymerization inhibitor or polymerization retarder can be used any liquid capable of dissolving these therein. Since phenol compound polymerization inhibitors such as, e.g., hydroquinone and methoquinone are soluble in water, acetic acid, (meth)acrylic acid, (meth)acrylic esters, aromatic compounds, ketones, alcohols, mixtures of one or more of these, and the like, a suitable one may be selected from these and used.

In particular, methoquinone is used in many cases as a polymerization inhibitor for (meth)acrylic acid or esters thereof. Since methoquinone is soluble in (meth)acrylic acid or esters thereof, methoquinone is generally used in such a manner that it is added to and dissolved in (meth)acrylic acid or an ester thereof without separately using a solvent.

An ambient gas suitable for (meth)acrylic acid or esters thereof preferably is a mixed gas which comprises air or oxygen and an incombustible gas and which has a regulated oxygen concentration. Examples of the incombustible gas include nitrogen, carbon dioxide, argon, and the like. In general, however, nitrogen gas is used.

The oxygen concentration in the mixed gas which comprises air or oxygen and an incombustible gas and is to be supplied as an ambient gas for (meth)acrylic acid or an ester thereof is preferably from 2 to 10%, especially from 5 to 8%, from the standpoints of polymerization inhibition and the prevention of explosive-composition formation. In case where the oxygen concentration in the mixed gas is lower than 2%, there is a possibility that polymerization reaction might occur. In case where the oxygen concentration therein exceeds 10%, there is a possibility that the compound being sealed might form an explosive composition. The reason why higher oxygen concentrations in the ambient gas are preferred for polymerization inhibition is that the polymerization inhibitor and/or polymerization retarder, e.g., methoquinone, added to (meth)acrylic acid or an ester thereof functions more effectively when oxygen is present in the (meth)acrylic acid or ester thereof.

Incidentally, easily polymerizable compounds such as (meth)acrylic acid or esters thereof absorb water contained in the ambient gas to come to have an elevated water content and this is causative of a decrease in product quality. For preventing such an increase in water content, the gases to be used for the mixed gas as an ambient gas desirably are dry gases having a dew point of from +10 to −50° C., preferably having a dew point of from −20 to −40° C. Consequently, especially when air is to be used, it is desirable to employ dry air having such a dew point, e.g., air for instrumentation.

In the invention, an ambient gas such as a mixed gas comprising an incombustible gas, e.g., nitrogen gas, and either air or oxygen is supplied to a production apparatus or storage apparatus for a compound to be sealed, e.g., (meth) acrylic acid or an ester thereof, in the following manner. A gas consumption in the gas-phase part is detected and, based on this detection value, the ambient gas is supplied from a supply line to the gas-phase part in an amount compensating for the consumption. Furthermore, a gas consumption in the supply line is detected and, based on this detection value, the ambient gas is supplied from a gas supply source to the supply line in an amount compensating for the consumption. The area to which the ambient gas is to be supplied may be any of the gas-phase part and/or liquid-phase part of the production apparatus or storage apparatus. From the standpoint of polymerization prevention, it is preferred to supply to the liquid-phase part.

Incidentally, the production apparatus or storage apparatus for a compound to be sealed include a variety of apparatus in which a compound to be sealed is handled, such as a storage tank for an unpurified compound to be sealed or purified compound to be sealed, a storage apparatus for high-boiling bottoms from a purification column or high-boiling treatment column, such as ones containing a compound to be sealed, e.g., (meth)acrylic acid or an ester thereof, in an amount of, e.g., 10% by weight or larger, a mixing vessel for mixing a polymerization inhibitor or the like with the compound to be sealed, and other facilities including transfer lines.

The method of supplying an ambient gas of the invention will be explained below in more detail by reference to the drawings.

Figure 2:
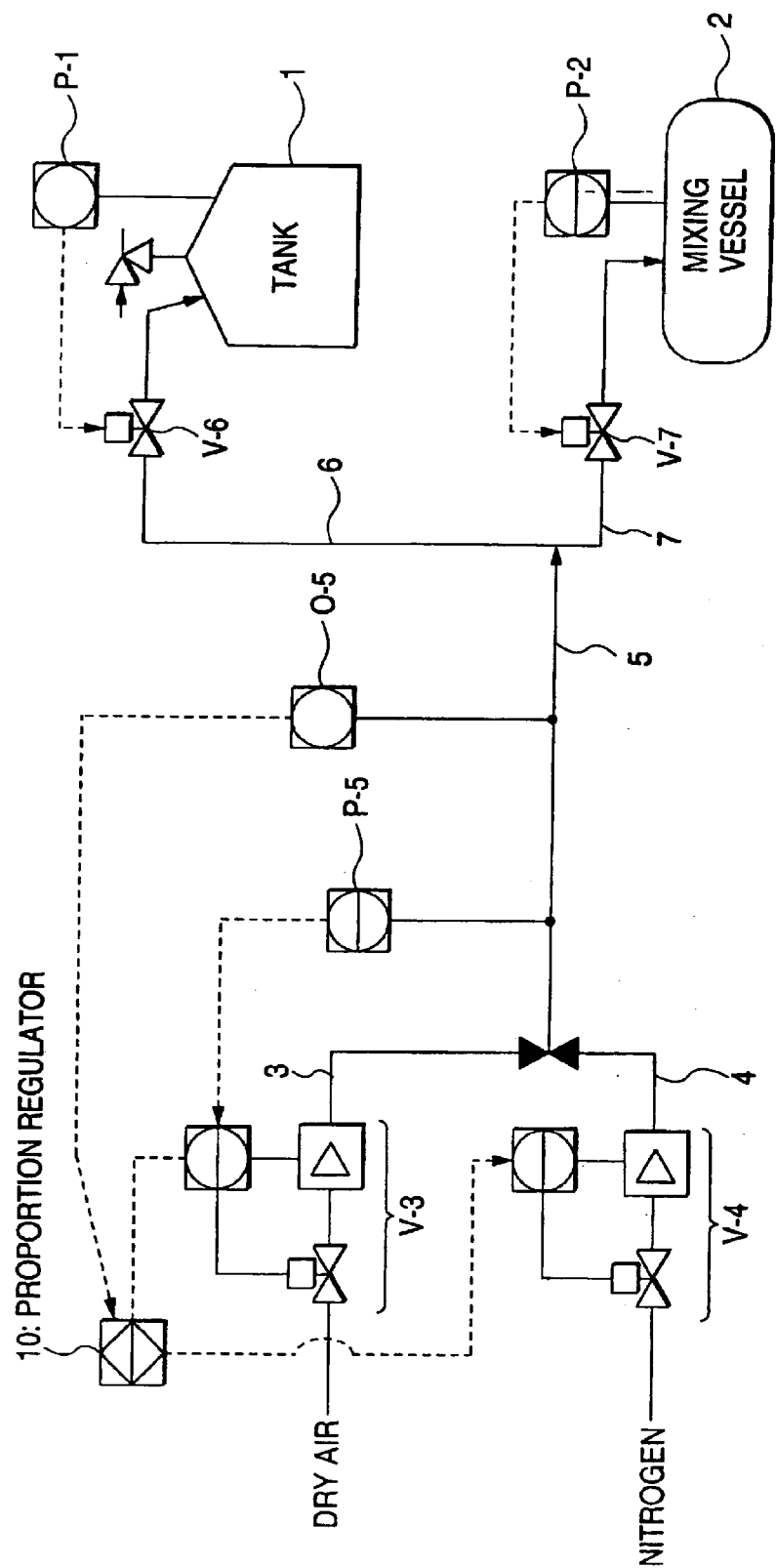
FIG. 2 is a system diagram showing another embodiment of the method of supplying an ambient gas of the invention.

FIGS. 1 and 2 are system diagrams showing embodiments of the method of supplying an ambient gas of the invention. FIGS. 1 and 2 illustrate methods in which a mixed gas composed of dry air and nitrogen gas is supplied as a sealing ambient gas to a storage tank for (meth)acrylic acid or an ester thereof (e.g., methyl acrylate) and to a mixing vessel (e.g., a vessel for mixing methyl acrylate with methoquinone as a polymerization inhibitor) according to the method of the invention. However, it is a matter of course that the compound to be sealed, ambient gas, and mode of supplying the same in the invention should not be construed as being limited to those shown in the drawings in any way, unless they depart from the spirit of the invention.

In FIGS. 1 and 2, 1 denotes a tank and 2 denotes a mixing vessel. A mixed gas composed of dry air supplied through a piping 3 and nitrogen supplied through a piping 4 passes through a piping 5 and is supplied to the tank 1 and the mixing vessel 2 through branch pipings 6 and 7, respectively. A manometer P-1 which detects the pressure of the gas-phase part in the tank 1 has been disposed in the tank 1 so that an on-off valve V-6 disposed in the branch piping 6, through which the mixed gas in supplied to the tank 1, is opened/closed based on the results of the detection by this manometer P-1. Furthermore, a manometer P-2 which detects the pressure of the gas-phase part in the mixing vessel 2 has been disposed in the mixing vessel 2 so that an on-off valve V-7 disposed in the branch piping 7, through which the mixed gas is supplied to the mixing vessel 2, is opened/closed based on the results of the detection by this manometer P-2. Moreover, a manometer P-5 which detects the pressure in the mixed-gas supply piping 5 has been disposed in this piping 5 so that the degree of opening of a flow control valve V-3 disposed in the dry-air supply piping 3 is regulated based on the results of the detection by this manometer P-5. A proportion regulator 10 has been further disposed which regulates, according to the degree of opening of the flow control valve V-3, the degree of opening of a flow control valve V-4 disposed in the nitrogen supply piping 4.

In the method shown in FIG. 1, a mixed gas having a given oxygen concentration obtained by regulating a flow rate proportion by the proportion regulator 10 is supplied to the tank 1 and mixing vessel 2 based on the mixed-gas consumptions in the tank 1 and mixing vessel 2 in amounts compensating for the gas consumptions.

Namely, in the case where an ambient gas in the gas-phase part in the tank 1 or mixing vessel 2 is discharged and consumed and the fact that the pressure of the gas-phase part in the tank 1 or mixing vessel 2 has thus decreased to below a set pressure is detected by the manometer P-1 or P-2, the on-off valve V-6 or V-7 is opened based on these results to supply a mixed gas to the tank 1 or mixing vessel 2 in a given amount. In the case where the fact that the pressure of the gas-phase part in the tank 1 or mixing vessel 2 has reached the set pressure due to the mixed-gas supply is detected by the manometer P-1 or P-2, the on-off valve V-6 or V-7 is closed based on these results to stop the supply of the mixed gas.

Incidentally, the tank 1 and the mixing vessel 2 each have been provided with a vent piping having a breather valve. In case where the pressure of the gas-phase part in the tank 1 and mixing vessel 2 exceeds a set pressure, this breather valve works to release the excess gas as a vent gas. The gas released is treated according to need and then finally treated with an incinerator or the like and thereby converted to harmless and odorless substances.

The pressure in the mixed-gas supply piping 5 decreases according to the supply of a mixed gas to the tank 1 or mixing vessel 2. Consequently, in the case where the pressure in the piping 5, which is detected by the manometer P-5, has decreased to below a set pressure, the degree of opening of the flow control valve V-3 disposed in the dry-air supply piping 3 is increased based on the detection results to supply dry air. Simultaneously therewith, the degree of opening of the flow control valve V-4 disposed in the nitrogen supply piping 4 is regulated by the proportion regulator 10 so as to be in proportion to the degree of opening of the flow control valve V-3 and to result in a given proportion. Thus, dry air and nitrogen are supplied to the mixed-gas supply piping 5 in a given flow rate ratio and, hence, so as to result in a mixed gas having a given oxygen concentration. When the fact that the pressure in the mixed-gas supply piping 5 has reached the set pressure due to the supply of the mixed gas having a given oxygen concentration is detected by the manometer P-5, then the flow control valve V-3 is closed and the flow control valve V-4 also is closed simultaneously to stop the supply of dry air and nitrogen.

The method shown in FIG. 2 is the same as the method shown in FIG. 1 except the following. An oxygen concentration meter O-5 has been further disposed in the mixed-gas supply piping 5 so that the ratio of the flow rate of dry air to that of nitrogen is finely regulated based on the results of detection by the oxygen concentration meter O-5. In this method, the oxygen concentration in the mixed gas can hence be more precisely regulated.

In the method shown in FIG. 2, when the pressure in the tank 1 or mixing vessel 2 has decreased, a mixed gas is supplied to the tank 1 or mixing vessel 2 in the same manner as in the method shown in FIG. 1. Simultaneously with this, when the fact that the pressure in the mixed-gas supply piping 5 has decreased to below a set pressure is detected by the manometer P-5, the degree of opening of the flow control valve V-3 is increased to supply dry air and nitrogen is supplied in an amount proportional to the flow rate of the dry air, as in the method shown in FIG. 1. In addition, in the method shown in FIG. 2, the oxygen concentration in the mixed gas in the mixed-gas supply piping 5 is detected by the oxygen concentration meter O-5 and the degree of opening of the flow control valve V-4 is finely regulated based on the results of the detection so that the oxygen concentration in the mixed gas becomes a given concentration. Because of this, the oxygen concentration in the mixed gas can be even more precisely regulated.

Although a mixed gas composed of dry air and nitrogen is supplied in FIGS. 1 and 2, oxygen may be used in place of the dry air. In this case, the nitrogen concentration in the mixed gas may be measured in place of the oxygen concentration therein. Furthermore, in the method shown in FIG. 2, it is possible that the amounts of dry air and nitrogen to be supplied are regulated based only on the results of measurements with the oxygen concentration meter.

While the invention has been described in detail and with reference to specific embodiments thereof, it will be apparent to one skilled in the art that various changes and modifications can be made therein without departing from the spirit and scope thereof.

This application is based on a Japanese patent application filed on Nov. 21, 2001 (Application No. 2001-356288), the contents thereof being herein incorporated by reference.

INDUSTRIAL APPLICABILITY

As described above in detail, according to the ambient-gas supply method of the invention, an ambient gas having a given composition can be stably supplied to a production apparatus or storage apparatus for a compound necessitating strict ambient gas regulation during the production, storage, or handling thereof, such as (meth)acrylic acid or an ester thereof which are easily polymerizable and form an explosive composition at ordinary temperature, in a manner not influenced by fluctuations in the amount of the gas used.

What is claimed is:

1. A method of supplying an ambient gas from a gas supply source through a supply line to an apparatus containing at least one compound comprising:

first detecting a gas consumption in a gas-phase part in the apparatus;

supplying, based on the results of this detection, the ambient gas from the supply line in an amount compensating for the gas consumption in the gas-phase part that;

further detecting a gas consumption in the supply line; and, supplying, based on the results of this detection, the ambient gas to the supply line from the gas supply source in an amount compensating for the gas consumption in the supply line.

2. The method of supplying an ambient gas as claimed in claim 1, characterized in that the ambient gas is a mixed gas comprising an incombustible gas and either air or oxygen.

3. The method of supplying an ambient gas as claimed in claim 2, characterized in that the incombustible gas is nitrogen gas.

4. The method of supplying an ambient gas as claimed in any one of claims 1 to 3, characterized in that the compound is a compound which is easily polymerizable and capable of forming an explosive composition at from 0 to 50° C.

5. The method of supplying an ambient gas as claimed in claim 1, characterized in that the compound is an easily polymerizable compound which is inhibited from polymerizing by oxygen present in the ambient gas.

6. The method of supplying an ambient gas as claimed in claim 4, characterized in that the compound is methyl(meth)acrylate, ethyl(meth)acrylate, or butyl(meth)acrylate.

7. The method of supplying an ambient gas as claimed in claim 1, characterized in that the gas consumption in the gas-phase part is detected by measuring a gas pressure of the gas-phase part.

8. The method of supplying an ambient gas as claimed in claim 1, characterized in that the gas consumption in the supply line is detected by measuring a gas pressure in the supply line.

9. The method of supplying an ambient gas as claimed in claim 2, characterized in that an incombustible gas and either air or oxygen are separately supplied to the supply line so as to result in a given proportion.

10. The method as claimed in claim 9, characterized in that the ratio of the flow rate of the incombustible gas to that of the air or oxygen is regulated.

11. The method as claimed in claim 9 or 10, characterized in that the incombustible-gas concentration or oxygen concentration in the gas being supplied to the supply line is regulated.

12. The method as claimed in claim 1, characterized in that the ambient gas has an oxygen concentration of from 2 to 10%.

* * * * *